United States Patent
Yamamoto

(10) Patent No.: US 11,583,247 B2
(45) Date of Patent: Feb. 21, 2023

(54) ACOUSTIC WAVE IMAGE GENERATING APPARATUS AND CONTROL METHOD THEREOF

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 777 days.

(21) Appl. No.: 15/383,158

(22) Filed: Dec. 19, 2016

(65) Prior Publication Data

US 2017/0100093 A1  Apr. 13, 2017

Related U.S. Application Data

(63) Continuation of application No. PCT/JP2015/065005, filed on May 26, 2015.

(30) Foreign Application Priority Data

Sep. 10, 2014  (JP) .............................. JP2014-183748

(51) Int. Cl.
*A61B 8/14* (2006.01)
*A61B 8/00* (2006.01)
(Continued)

(52) U.S. Cl.
CPC .............. *A61B 8/14* (2013.01); *A61B 8/4483* (2013.01); *A61B 8/4488* (2013.01);
(Continued)

(58) Field of Classification Search
CPC ....... A61B 8/14; A61B 8/4483; A61B 8/5207; A61B 8/461; A61B 8/5215; A61B 8/5269; A61B 8/54; G01S 15/8915; G01S 7/52026
See application file for complete search history.

(56) References Cited

U.S. PATENT DOCUMENTS 5,570,691 A * 11/1996 Wright ................ G01S 7/52049
600/447
5,910,118 A * 6/1999 Kanda ................. G01S 15/8981
600/455
(Continued)

FOREIGN PATENT DOCUMENTS

JP       2012-217583 A     11/2012
JP       2014-30715 A       2/2014

OTHER PUBLICATIONS

English Translation of the International Preliminary Report on Patentability and Written Opinion dated Mar. 14, 2017 in PCT/JP2015/065005.
(Continued)

*Primary Examiner* — Boniface Ngathi N
*Assistant Examiner* — Milton Truong
(74) *Attorney, Agent, or Firm* — Birch, Stewart, Kolasch & Birch, LLP

(57) ABSTRACT

There are provided an acoustic wave image generating apparatus for generating a B-mode image having a fixed brightness and a control method thereof. First brightness information (81) indicating the brightness of a first B-mode image in the depth direction of the subject is generated. Positional deviation correction is performed on an acoustic wave echo signal having a positional deviation between the focusing position of acoustic waves and the observation target position, and second brightness information (82) indicating the brightness in the depth direction of the subject is generated from a superposition signal obtained by superimposing an acoustic wave echo signal for which the positional deviation has been corrected and an acoustic wave echo signal without positional deviation. The brightness of the first B-mode image is corrected based on the first
(Continued)

brightness information and the second brightness information.

10 Claims, 11 Drawing Sheets

(51) Int. Cl.
　　　G01S 7/52　　　　(2006.01)
　　　G01S 15/89　　　(2006.01)
　　　A61B 8/08　　　　(2006.01)
(52) U.S. Cl.
　　　CPC .......... *A61B 8/5207* (2013.01); *A61B 8/5215* (2013.01); *A61B 8/5269* (2013.01); *G01S 7/52026* (2013.01); *G01S 15/8915* (2013.01); *A61B 8/461* (2013.01); *A61B 8/54* (2013.01)

(56) References Cited

U.S. PATENT DOCUMENTS

| | | | | |
|---|---|---|---|---|
| 2008/0114245 A1* | 5/2008 | Randall | ..................... | A61B 8/42 600/447 |
| 2009/0326377 A1* | 12/2009 | Hirama | ............... | G01S 7/52046 600/447 |
| 2011/0237950 A1* | 9/2011 | Meng | .................. | G01S 15/8909 600/447 |
| 2013/0030296 A1* | 1/2013 | Miyaki | ............... | G01S 7/52033 600/442 |
| 2013/0113938 A1* | 5/2013 | Miyaki | .................... | H04N 5/30 348/163 |
| 2015/0141831 A1 | 5/2015 | Yamamoto | | |
| 2015/0286044 A1* | 10/2015 | Rout | .................. | G02B 27/0081 348/79 |
| 2016/0174938 A1* | 6/2016 | Takano | .................... | A61B 8/14 600/459 |

OTHER PUBLICATIONS

International Search Report Issued in PCT/JP2015/065005, dated Aug. 18, 2015.

Written Opinion of the International Searching Authority Issued in PCT/JP2015/065005 (PCT/ISA/237), dated Aug. 18, 2015.

* cited by examiner

ACOUSTIC WAVE IMAGE GENERATING APPARATUS AND CONTROL METHOD THEREOF

CROSS-REFERENCE TO RELATED APPLICATIONS

This application is a Continuation of PCT International Application No. PCT/JP2015/065005 filed on May 26, 2015, which claims priority under 35 U.S.C. §119(a) to Japanese Patent Application No. 2014-183748 filed Sep. 10, 2014. Each of the above application(s) is hereby expressly incorporated by reference, in its entirety, into the present application.

BACKGROUND OF THE INVENTION

1. Field of the Invention

The present invention relates to an acoustic wave image generating apparatus and a control method thereof.

2. Description of the Related Art

Generally, an ultrasound image is bright in the vicinity of a position where ultrasound waves are focused, and becomes dark as a distance from the position increases. For this reason, transmitted sound waves of the ultrasound beam are calculated, and different gains are adjusted for each depth based on the calculation result (JP2012-217583A). In addition, there is a method of generating a piece of element data from a plurality of pieces of element data in consideration of propagation time using element data before phasing addition and generating an image by performing phasing addition (JP2014-030715A). According to this, it is possible to obtain an image with little gain deviation for each depth.

SUMMARY OF THE INVENTION

In the method disclosed in JP2012-217583A, however, since a calculation result calculated based on the ideal state is used, actual deviation occurs. Accordingly, gain adjustment for each depth may not be able to be performed accurately. In the method disclosed in JP2014-030715A, since the calculation load is large, the frame rate of the ultrasound image may be reduced.

It is an object of the present invention to relatively easily obtain an acoustic wave image having a fixed brightness for each depth.

An acoustic wave image generating apparatus (ultrasound image generating apparatus) according to the present invention comprises: an acoustic wave probe in which a plurality of acoustic wave transducers are arranged in at least one direction; a driving device (driving means) for performing processing for transmitting acoustic waves, which converge on a focusing position, to a subject from the acoustic wave transducers to be driven while sequentially updating the acoustic wave transducers to be driven; a first acoustic wave image generation device (first acoustic wave image generation means) for generating a first acoustic wave image, which shows a brightness of a cross section of the subject, from acoustic wave echo signals that are output from the acoustic wave transducers due to the acoustic wave transducers receiving acoustic wave echoes at an observation target position of the subject obtained based on the driving of the acoustic wave transducers by the driving device; a first brightness information generation device (first brightness information generation means) for generating first brightness information indicating a brightness of the first acoustic wave image in a depth direction of the subject; a positional deviation correction device (positional deviation correction means) for correcting, for the acoustic wave echo signal having a positional deviation between the focusing position and the observation target position in the one direction, the positional deviation according to positions of the acoustic wave transducers driven by the driving device; a second brightness information generation device (second brightness information generation means) for generating second brightness information, which indicates a brightness in the depth direction of the subject, from a superposition signal obtained by superimposing the acoustic wave echo signal for which the positional deviation has been corrected by the positional deviation correction device and the acoustic wave echo signal without the positional deviation; and a brightness correction device (brightness correction means) for correcting a brightness of the first acoustic wave image generated by the first acoustic wave image generation device based on the first brightness information generated by the first brightness information generation device and the second brightness information generated by the second brightness information generation device.

The present invention also provides a control method suitable for the acoustic wave image generating apparatus. That is there is provided a control method of an acoustic diagnostic apparatus comprising an acoustic wave probe in which a plurality of acoustic wave transducers are arranged in at least one direction, The control method includes: causing a driving device (driving means) to perform processing for transmitting acoustic waves, which converge on a focusing position, to a subject from the acoustic wave transducers to be driven while sequentially updating the acoustic wave transducers to be driven; causing an acoustic wave image generation device (acoustic wave image generation means) to generate an acoustic wave image, which shows a brightness of a cross section of the subject, from acoustic wave echo signals that are output from the acoustic wave transducers due to the acoustic wave transducers receiving acoustic wave echoes at an observation target position of the subject obtained based on the driving of the acoustic wave transducers by the driving device; causing a first brightness information generation device (first brightness information generation means) to generate first brightness information indicating a brightness of the first acoustic wave image in a depth direction of the subject; causing a positional deviation correction device (positional deviation correction means) to correct, for the acoustic wave echo signal having a positional deviation between the focusing position and the observation target position in the one direction, the positional deviation according to positions of the acoustic wave transducers driven by the driving device; causing a second brightness information generation device (second brightness information generation means) to generate second brightness information, which indicates a brightness in the depth direction of the subject, from a superposition signal obtained by superimposing the acoustic wave echo signal for which the positional deviation has been corrected by the positional deviation correction device and the acoustic wave echo signal without the positional deviation; and causing a brightness correction device (brightness correction means) to correct a brightness of the acoustic wave image generated by the acoustic wave image generation device based on the first brightness information generated by the first brightness information generation device and the second brightness information generated by the second brightness information generation device.

The brightness correction device may comprise a correction coefficient calculation device (correction coefficient calculation means) for calculating a correction coefficient, which is for correcting the brightness of the first acoustic wave image generated by the first acoustic wave image generation device, based on the first brightness information generated by the first brightness information generation device and the second brightness information generated by the second brightness information generation device. In this case, it is preferable that the brightness of the first acoustic wave image generated by the first acoustic wave image generation device is corrected using the correction coefficient calculated by the correction coefficient calculation device.

The number of acoustic wave transducers driven in a case where the first acoustic wave image is generated by the first acoustic wave image generation device may be different from the number of acoustic wave transducers driven in a case where correction of positional deviation is performed by the positional deviation correction device.

The positional deviation correction of the positional deviation correction device and superposition of the acoustic wave echo signal for which the positional deviation has been corrected and the acoustic wave echo signal without the positional deviation may be performed every one or more of the ultrasound transducers in the one direction.

Superposition of the acoustic wave echo signals for which the positional deviation has been corrected and acoustic wave echo signals without the positional deviation may be performed after giving a weighting to at least some of the acoustic wave echo signals for which the positional deviation has been corrected and acoustic wave echo signals without the positional deviation.

For example, the correction coefficient calculation device calculates a correction coefficient, based on a brightness of a portion corresponding to the focusing position, in the first acoustic wave image generated by the first acoustic wave image generation device.

A second acoustic wave image generation device (second acoustic wave image generation means) for generating a second acoustic wave image showing a brightness of the subject from the superposition signal may be further comprised.

According to the present invention, the first acoustic wave image showing the brightness of the cross section of the subject is generated from acoustic wave echo signals that are output from the acoustic wave transducers due to the acoustic wave transducers receiving acoustic wave echoes at the observation target position of the subject. The first brightness information indicating the brightness of the first acoustic wave image in the depth direction of the subject is generated. In addition, for the acoustic wave echo signal having a positional deviation between the focusing position of acoustic waves and the observation target position, the positional deviation is corrected according to the positions of the acoustic wave transducers. The second brightness information indicating the brightness in the depth direction of the subject is generated from the superposition signal obtained by superimposing the corrected acoustic wave echo signal and the acoustic wave echo signal without positional deviation. The brightness of the first acoustic wave image is corrected based on the first brightness information and the second brightness information that have been generated. Due to this correction, the brightness of the first acoustic wave image is fixed.

DESCRIPTION OF THE PREFERRED EMBODIMENTS

Figure 1:
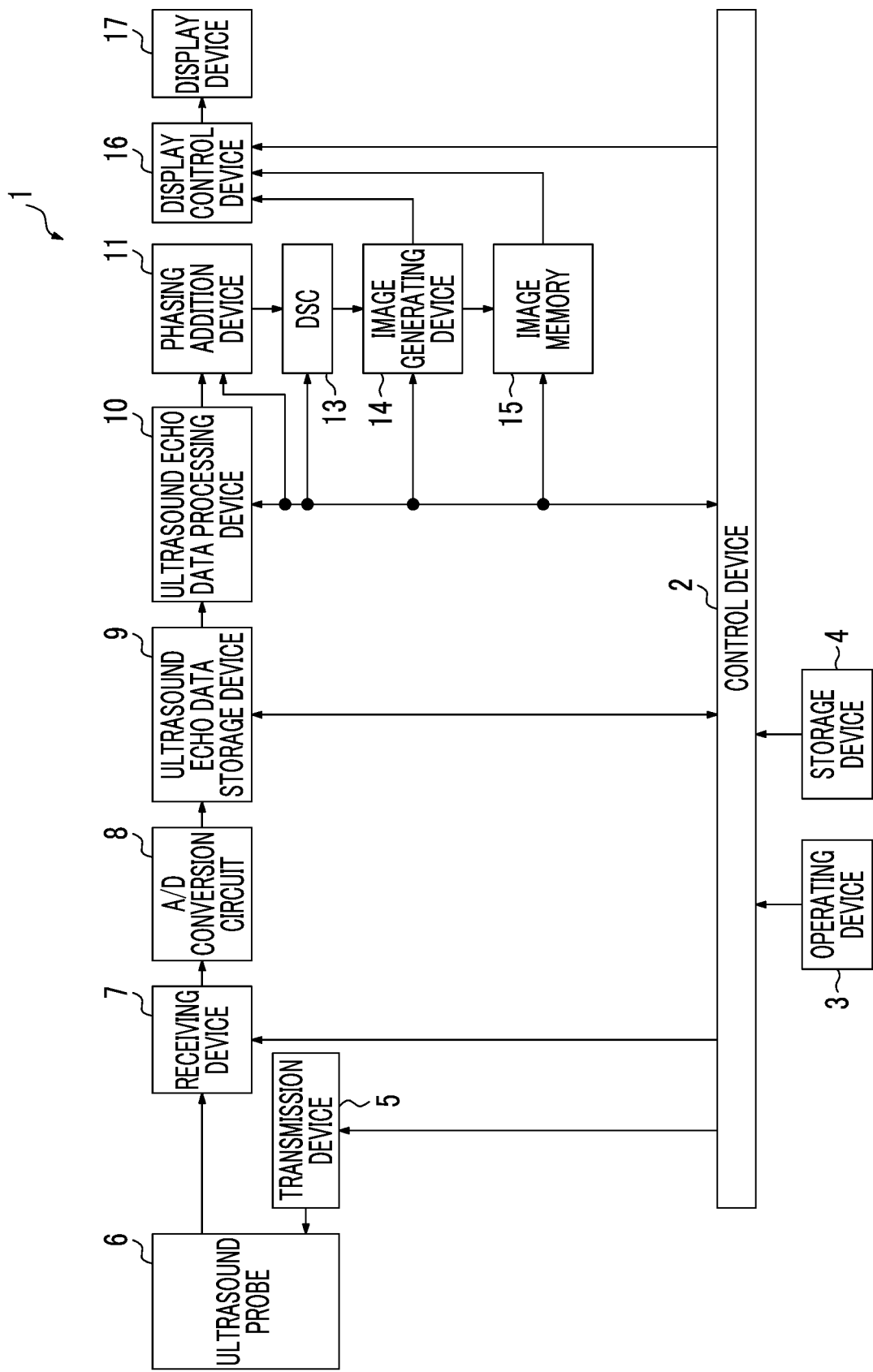
FIG. 1 is a block diagram showing the electrical configuration of an ultrasound diagnostic apparatus.

FIG. 1 shows an embodiment of the present invention, and is a block diagram showing the electrical configuration of an ultrasound diagnostic apparatus (acoustic wave image generating apparatus).

In the present embodiment, an ultrasound wave is used as an acoustic wave. However, as long as an appropriate frequency is selected according to an object to be examined, measurement conditions, and the like, an acoustic wave having an audible frequency may be used without being limited to the ultrasound wave. In addition, not only can the present invention be used for diagnosing the disease of a person as a subject, but also the present invention can be used to examine the contents of walls, piping, and the like by generating an acoustic wave image (ultrasound image).

In the ultrasound diagnostic apparatus according to the present embodiment, in addition to a first B-mode image (first acoustic wave image) having normal image quality, a high-quality second B-mode image (second acoustic wave image) can be generated by processing called so-called multi-line processing. However, the high-quality second B-mode image does not necessarily need to be generated. In particular, in the present embodiment, not an image having a brightness that changes according to the depth direction of the subject but a first B-mode image having a fixed brightness regardless of the depth direction is generated.

First, processing in a case where the second B-mode image is generated will be described.

The overall operation of an ultrasound diagnostic apparatus 1 is controlled by a control device 2.

An operating device 3, which is operated by a technician or the like who operates the ultrasound diagnostic apparatus 1, and a storage device 4, in which predetermined data and the like are stored, are connected to the control device 2.

An ultrasound probe 6 is included in the ultrasound diagnostic apparatus 1. A plurality of ultrasound transducers are included in the ultrasound probe 6.

A control signal output from the control device 2 is supplied to a transmission device 5. Then, an electrical pulse is supplied to each ultrasound transducer of the ultrasound probe 6 from the transmission device 5. The electrical pulse is converted into an ultrasound pulse by the ultrasound transducer, the ultrasound pulse propagates through the body of a subject, and the ultrasound echo returns to the ultrasound probe 6.

The ultrasound echo is converted into an electrical signal (ultrasound echo signal) by the ultrasound transducer.

FIGS. 2 to 11 show a state in which an ultrasound pulse is output from the ultrasound probe 6 and an ultrasound echo signal is obtained.

Figure 2:
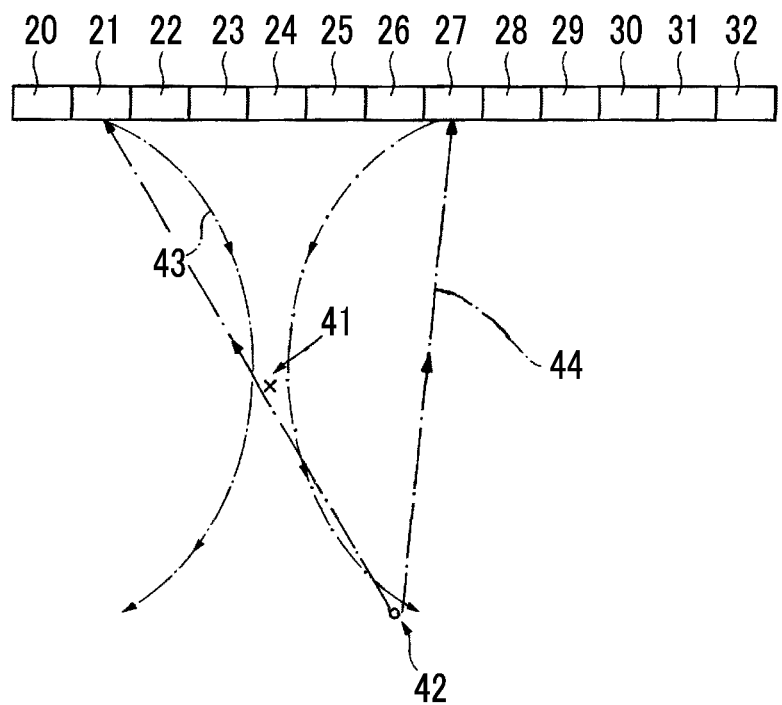
FIG. 2 shows the transmission of ultrasound pulses and the reception of ultrasound echoes.
Figure 4:
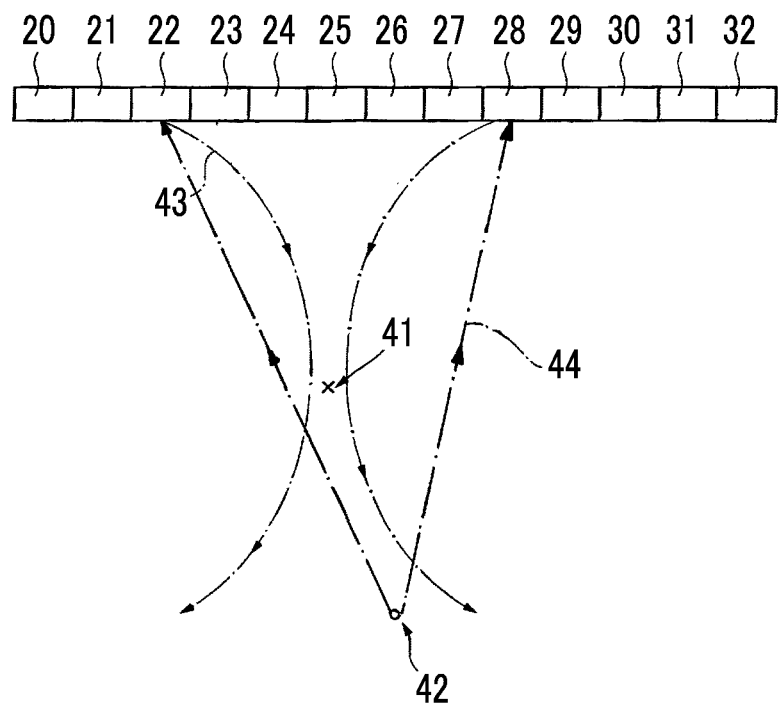
FIG. 4 shows the transmission of ultrasound pulses and the reception of ultrasound echoes.
Figure 6:
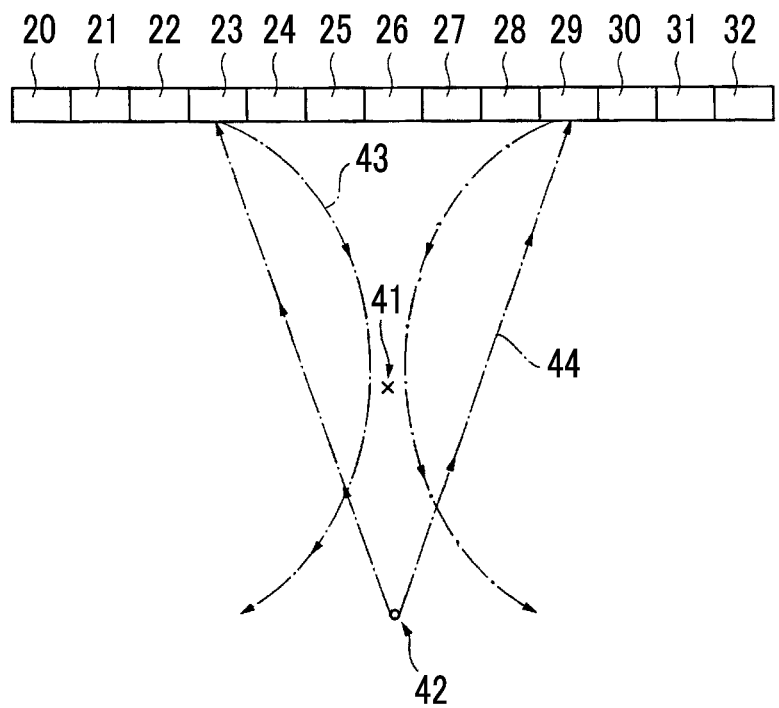
FIG. 6 shows the transmission of ultrasound pulses and the reception of ultrasound echoes.
Figure 8:
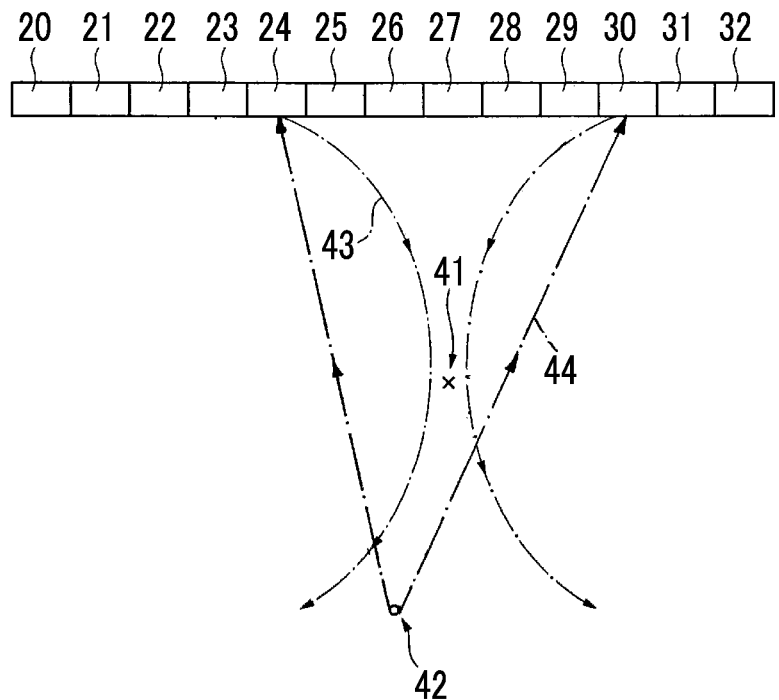
FIG. 8 shows the transmission of ultrasound pulses and the reception of ultrasound echoes.
Figure 10:
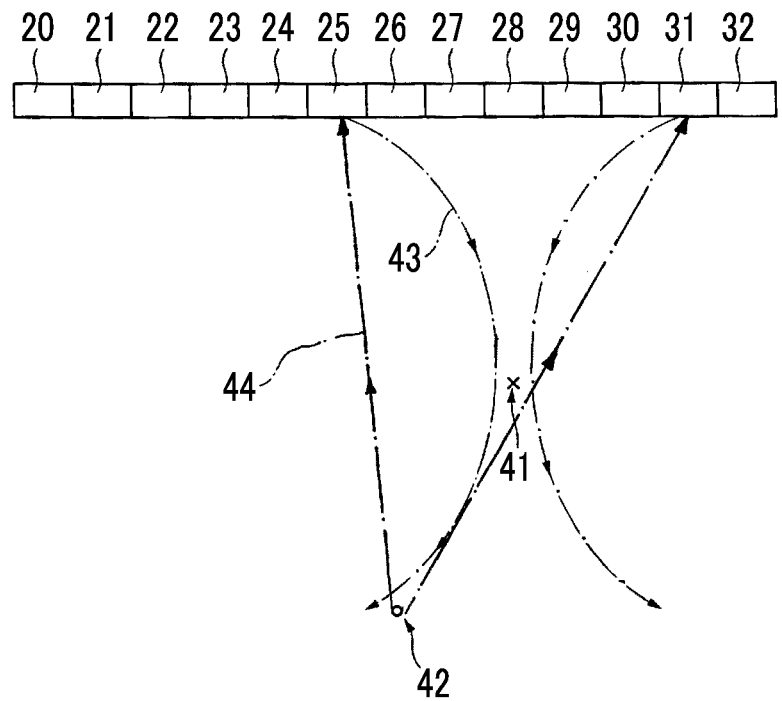
FIG. 10 shows the transmission of ultrasound pulses and the reception of ultrasound echoes.

FIG. 2 shows a state in which the ultrasound pulse 43 is output from the ultrasound transducers 21 to 27 among the ultrasound transducers 20 to 32 included in the ultrasound probe 6. FIG. 4 shows a state in which the ultrasound pulse 43 is output from the ultrasound transducers 22 to 28 among the ultrasound transducers 20 to 32 included in the ultrasound probe 6. FIG. 6 shows a state in which the ultrasound pulse 43 is output from the ultrasound transducers 23 to 29 among the ultrasound transducers 20 to 32 included in the ultrasound probe 6. FIG. 8 shows a state in which the ultrasound pulse 43 is output from the ultrasound transducers 24 to 30 among the ultrasound transducers 20 to 32 included in the ultrasound probe 6. FIG. 10 shows a state in which the ultrasound pulse 43 is output from the ultrasound transducers 25 to 31 among the ultrasound transducers 20 to 32 included in the ultrasound probe 6.

Thus, a plurality of ultrasound transducers (acoustic wave transducers) 20 to 32 arranged in at least one direction (or in a two-dimensional manner) are included in the ultrasound probe 6. By the control device 2 (a driving device), an ultrasound pulse (acoustic wave) 43 converging on the focusing position 41 is transmitted from ultrasound transducers to be driven while the ultrasound transducers to be driven, among the ultrasound transducers 20 to 32, are being updated in a sequential manner (while the ultrasound transducers to be driven are being changed in a sequential manner).

Referring to FIG. 6, it is assumed that the ultrasound pulse 43 is transmitted from the ultrasound transducers 23 to 29. The ultrasound pulse 43 is transmitted from the ultrasound transducers 23 to 29 so as to converge on the focusing position 41 at a predetermined distance in the transmission direction of the ultrasound transducer 26 (in FIG. 2, directly below the ultrasound transducer 26) located at the center of the ultrasound transducers 23 to 29. Since the ultrasound pulse 43 is transmitted with a delay according to the positions of the ultrasound transducers 23 to 29, the ultrasound pulse 43 converges on the focusing position 41. In the example shown in FIG. 6, the observation target position 42 (for example, a position where the medium changes in the subject) is present in the extension direction of the central ultrasound transducer 26 and the focusing position 41. For this reason, the ultrasound pulse 43 is emitted to the observation target position 42, and an ultrasound echo 44 is generated from the observation target position 42. The ultrasound echo 44 is received by the ultrasound transducers 23 to 29.

Figure 7:
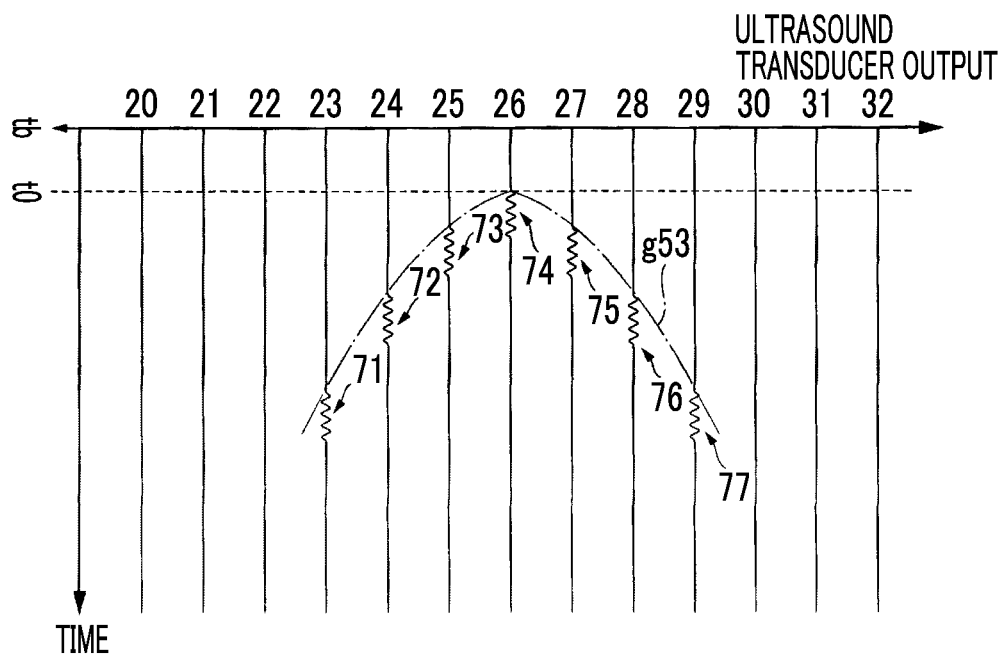
FIG. 7 shows an ultrasound echo signal.

FIG. 7 shows ultrasound echo signals 71 to 77 output from the ultrasound transducers 23 to 29 that have received the ultrasound echo 44. The horizontal axis indicates the position of the ultrasound transducer, and the vertical axis indicates the elapsed time from a time tb at which the ultrasound pulse 43 is output from the ultrasound transducer.

Since a difference between the propagation distances of the ultrasound pulse 43 and the ultrasound echo 44 occurs according to the positions of the ultrasound transducers 23 to 29, the output timing of the ultrasound echo signals 71 to 77 output from the ultrasound transducers 23 to 29 also differs depending on each ultrasound transducer. The propagation distance of the ultrasound pulse 43 output from the central ultrasound transducer 26 and the propagation distance of the ultrasound echo 44 of the central ultrasound transducer 26 from the observation target position 42 are the shortest. Accordingly, the ultrasound echo signal 74 is first output from the central ultrasound transducer 26 (time t0). The propagation distance of the ultrasound pulse 43 output from the ultrasound transducers 25 and 27 on both sides of the central ultrasound transducer 26 and the propagation distance of the ultrasound echo 44 of the ultrasound transducers 25 and 27 from the observation target position 42 are the second shortest. Accordingly, the ultrasound echo signals 73 and 75 are output from the ultrasound transducers 25 and 27 after the ultrasound echo signal 74. Similarly, the ultrasound echo signals 72 and 76 are then output from the ultrasound transducers 24 and 28. Finally, the ultrasound echo signals 71 and 77 are output from the ultrasound transducers 23 and 29. In FIG. 7 (the same for other diagrams), in order to show the ultrasound echo signals 71 to 77, an envelope of the ultrasound echo signals 71 to 77 is shown as an ultrasound echo signal group g53.

Referring to FIG. 2, it is assumed that the ultrasound pulse 43 is transmitted from the ultrasound transducers 21 to 27. If the ultrasound pulse 43 converges on the focusing position 41 and does not spread exceeding the width of one ultrasound transducer (in the case shown in FIG. 2, the ultrasound transducer 24), the ultrasound pulse 43 is not emitted to the observation target position 42 (for example, a position where the medium changes in the subject), which is not present in the extension direction of the central ultrasound transducer 24, among the ultrasound transducers 21 to 27 that transmit ultrasound waves, and the focusing position 41. Accordingly, no ultrasound echo 44 is generated from the observation target position 42. However, since the ultrasound pulse 43 spreads when the ultrasound pulse 43 passes the focusing position 41, the ultrasound pulse 43 is also emitted to the observation target position 42 that is not present in the extension direction of the central ultrasound transducer 24 and the focusing position 41. Accordingly, the ultrasound echo 44 is generated from the observation target position 42. The ultrasound echo 44 is received by the ultrasound transducers 21 to 27.

Figure 3:
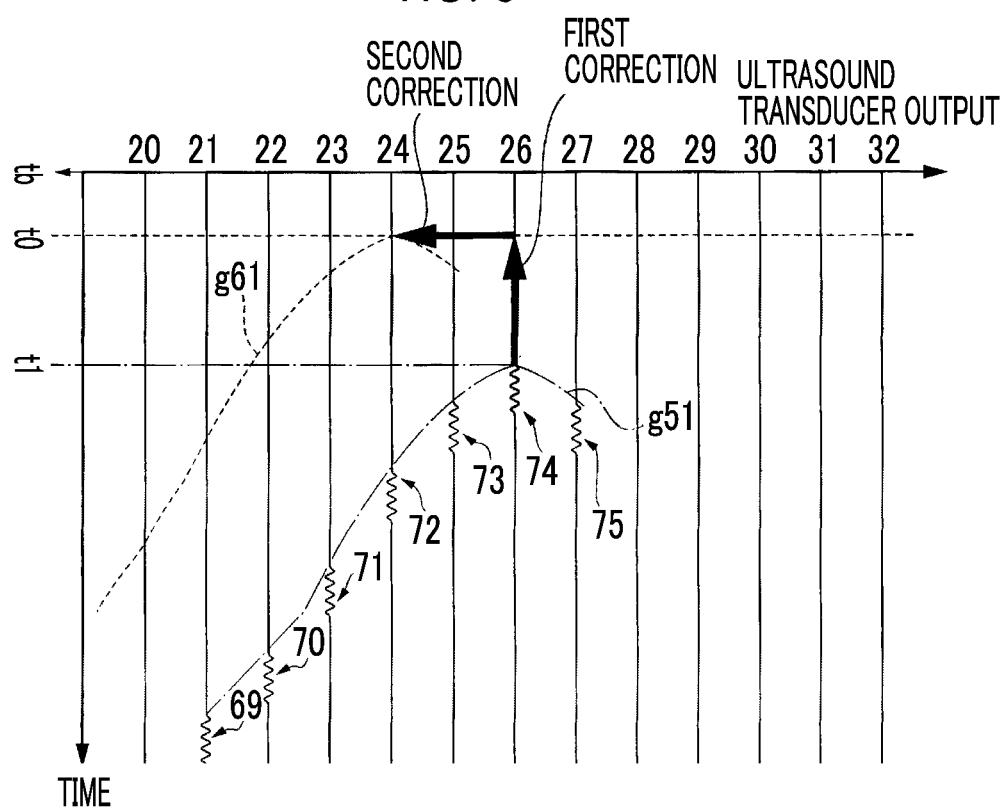
FIG. 3 shows an ultrasound echo signal.

FIG. 3 shows an ultrasound echo signal group g51 output from the ultrasound transducers 21 to 27 that receive the ultrasound echo 44. As shown in FIG. 7, the ultrasound echo signal group g51 is an envelope of ultrasound echo signals 69 to 75 output from the ultrasound transducers 21 to 27. Since the observation target position 42 is present in the output direction (in FIG. 2, directly below) of the ultrasound pulse 43 of the ultrasound transducer 26 among the ultrasound transducers 21 to 27 that receive the ultrasound echo 44, the ultrasound echo signal 74 is first output from the ultrasound transducer 26 (time t1). Then, the ultrasound echo signals 73 and 75 are output from the ultrasound transducers 25 and 27, respectively, and then the ultrasound echo signal 72 is output from the ultrasound transducer 24. In addition, the ultrasound echo signal 71 is output from the ultrasound transducer 23, the ultrasound echo signal 70 is output from the ultrasound transducer 22, and the ultrasound echo signal 69 is output from the ultrasound transducer 21. Since the focusing position 41 is not present between the observation target position 42 and the ultrasound transducer 26 that receives the ultrasound echo 44, the time t1 at which the ultrasound echo signal 74 is first output as shown in FIG. 3 is later than the time t0 at which the ultrasound echo signal 74 is first output as shown in FIG. 7.

Referring to FIG. 4, it is assumed that ultrasound transducers to be driven are updated and the ultrasound pulse 43 is transmitted from the ultrasound transducers 22 to 28. In the same manner as described with reference to FIG. 2, the ultrasound echo 44 from the observation target position 42 is received by the ultrasound transducers 22 to 28.

Figure 5:
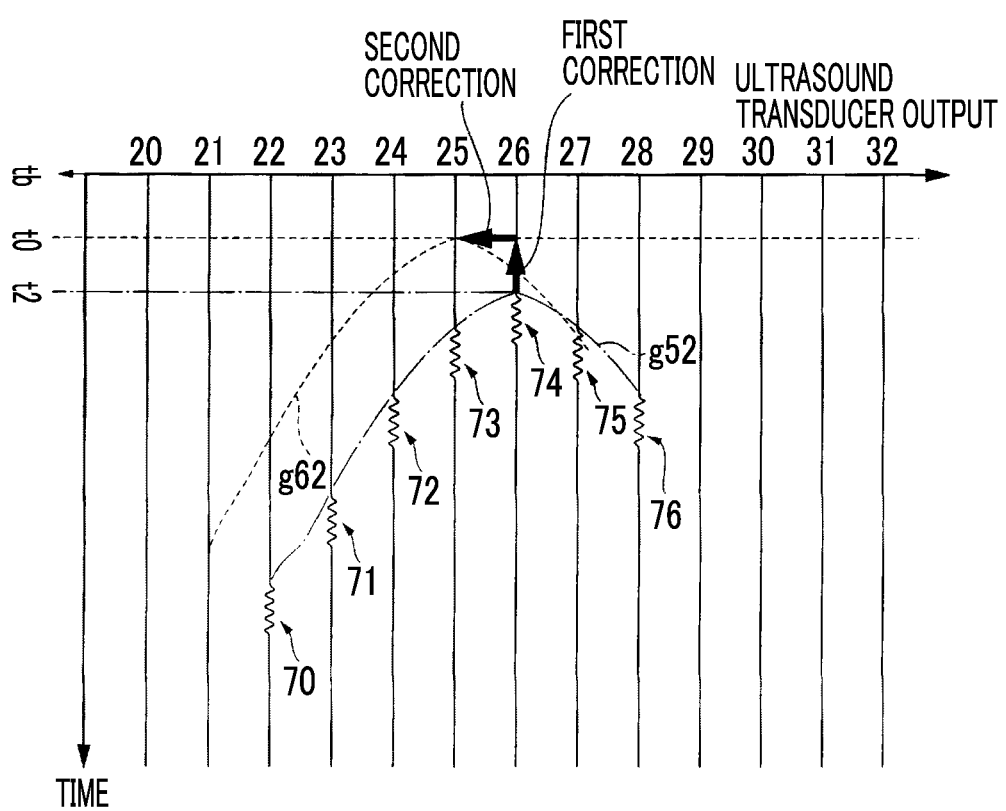
FIG. 5 shows an ultrasound echo signal.

Referring to FIG. 5, an ultrasound echo signal group g52 is obtained from the ultrasound transducers 22 to 28 in the same manner as in FIG. 3. As shown in FIG. 7, the ultrasound echo signal group g52 is also an envelope of ultrasound echo signals 70 to 76 output from the ultrasound transducers 22 to 28. The ultrasound echo signal 74 is first output from the ultrasound transducer 26 (time t2).

When ultrasound transducers to be driven are updated and the ultrasound pulse 43 is transmitted from the ultrasound transducers 23 to 29 as shown in FIG. 6, the operation is the same as that already described.

Referring to FIG. 8, it is assumed that ultrasound transducers to be driven are updated and the ultrasound pulse 43 is transmitted from the ultrasound transducers 24 to 30. The ultrasound echo 44 from the observation target position 42 is received by the ultrasound transducers 24 to 30.

Figure 9:
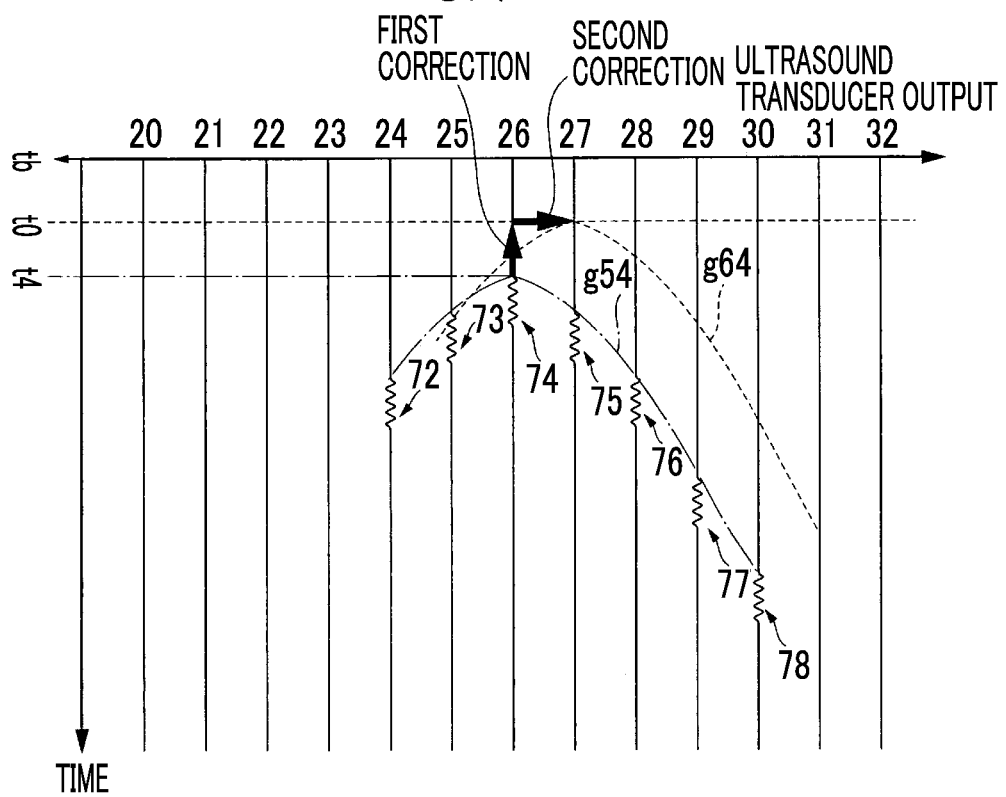
FIG. 9 shows an ultrasound echo signal.

Referring to FIG. 9, an ultrasound echo signal group g54 is obtained from the ultrasound transducers 24 to 30 in the same manner as in FIG. 3. As shown in FIG. 7, the ultrasound echo signal group g54 is also an envelope of ultrasound echo signals 72 to 78 output from the ultrasound transducers 24 to 30. In the same manner as described with reference to FIG. 2, the ultrasound echo signal 74 is first output from the ultrasound transducer 26 (time t4).

Referring to FIG. 10, it is assumed that ultrasound transducers to he driven are updated and the ultrasound pulse 43 is transmitted from the ultrasound transducers 25 to 31. The ultrasound echo 44 from the observation target position 42 is received by the ultrasound transducers 25 to 31.

Figure 11:
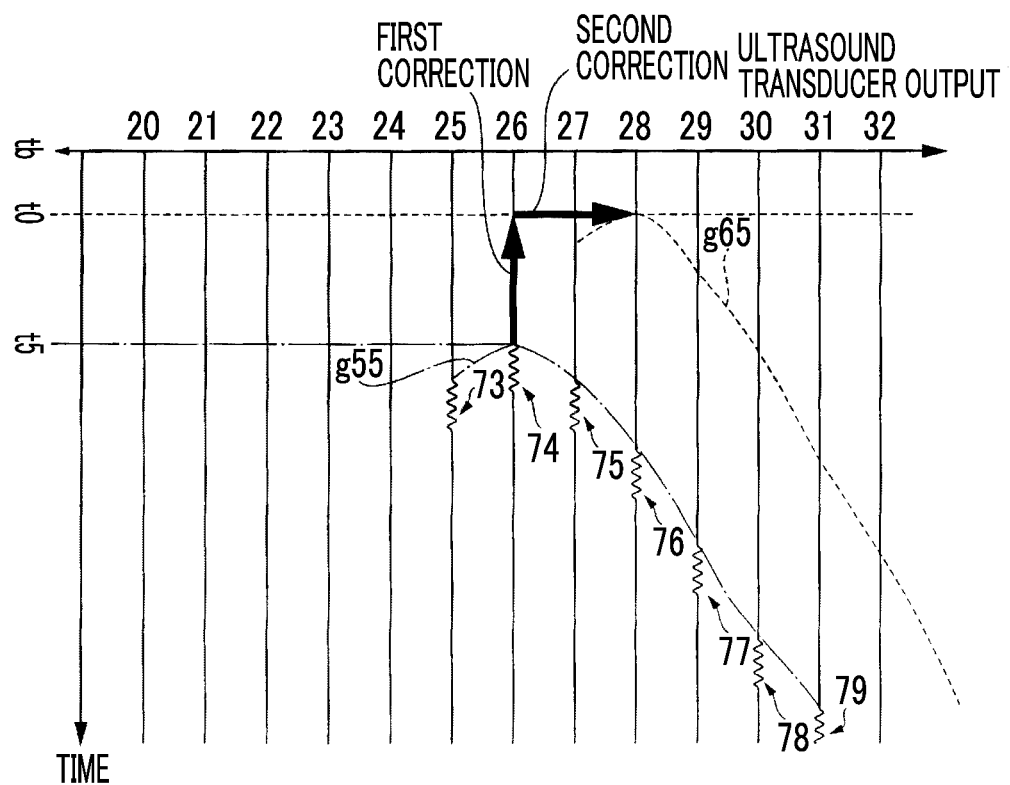
FIG. 11 shows an ultrasound echo signal.

Referring to FIG. 11, an ultrasound echo signal group g55 is obtained from the ultrasound transducers 25 to 31 in the same manner as in FIG. 2. As shown in FIG. 7, the ultrasound echo signal group g55 is also an envelope of ultrasound echo signals 73 to 79 output from the ultrasound transducers 25 to 31. The ultrasound echo signal 74 is first output from the ultrasound transducer 26 (time t5).

Referring to FIG. 1, the obtained ultrasound echo signals 69 to 79 are supplied to a receiving device 7. The ultrasound echo signals 69 to 79 or the like are amplified by the receiving device 7, and are converted into digital ultrasound echo signals by an A/D (analog/digital) conversion circuit 8. The ultrasound echo signals are supplied to an ultrasound echo data storage device 9 so as to be temporarily stored therein. The ultrasound echo signals are read from the ultrasound echo data storage device 9, and are input to an ultrasound echo data processing device 10.

In the ultrasound echo data processing device 10, among ultrasound echo signals (acoustic wave echo signals) that are output from ultrasound transducers (acoustic wave transducers) due to the ultrasound transducers (acoustic wave transducers) receiving the ultrasound echo (acoustic wave echo) of the observation target position 42 of the subject obtained based on the driving of the ultrasound transducers (acoustic wave transducers) by the control device 2 (a driving device), as shown in FIGS. 3, 5, 9, and 11, for an ultrasound echo signal (acoustic wave echo signal) having a positional deviation in one direction (horizontal direction) between the focusing position 41 and the observation target position 42, the positional deviation is corrected according to the position of the ultrasound transducer to be driven (a positional deviation correction device).

As will be described later, the correction of positional deviation is to generate an ultrasound echo signal obtained in a case where it is assumed that the observation target position 42 is present on the extension line of the focusing position 41 and the ultrasound transducer 24 located at the center of the ultrasound transducers 21 to 27 that receive the ultrasound echo 44 from the observation target position 42.

Referring to FIG. 3, in the ultrasound echo data processing device 10, as shown in FIG. 7, first correction is performed in order to correct the delay time so that the ultrasound echo signal group g51 is output from the ultrasound transducer 26 at the time t0, and second correction is performed in order to shift the apex of the ultrasound echo signal group g51 so that the one-direction positional deviation between the focusing position 41 and the observation target position 42 is eliminated. The positional deviation in one direction is a deviation between the focusing position 41 and the observation target position 42 in one direction. The correction of the positional deviation in one direction is to generate an ultrasound echo signal, which can be obtained in a case where there is no positional deviation in one direction, in a case where there is a positional deviation in one direction between the focusing position 41 and the observation target position 42 as shown in FIG. 2 (in a case where the focusing position 41 and the observation target position 42 are not present on a straight line in a direction perpendicular to the one direction). In the case shown in FIG. 2, the focusing position 41 and the observation target position 42 are shifted from each other by a distance of two ultrasound transducers in one direction. Accordingly, the ultrasound echo signal group g51 is shifted by the distance of two ultrasound transducers in a direction opposite to the one direction so that the deviation of the distance is eliminated. A combination of the first correction and the second correction is positional deviation correction (a positional deviation correction device). Therefore, as shown in FIG. 3, the ultrasound echo signal group g51 is corrected to an ultrasound echo signal group g61 as shown by the dotted line. Thus, in the ultrasound echo data processing device 10, among ultrasound echo signals (ultrasound echo data) that are output from the ultrasound transducers 21 to 27 due to the ultrasound transducers 21 to 27 receiving the ultrasound echo 44 of the observation target position 42 of the subject obtained based on the driving of the ultrasound transducers by the control device 2 (a driving device), for an ultrasound echo signal (ultrasound echo data) having a positional deviation in one direction between the focusing position 41 and the observation target position 42, the positional deviation is corrected according to the position of the ultrasound transducer to be driven by the control device 2.

The delay time in the first correction can be calculated as follows.

Figure 12:
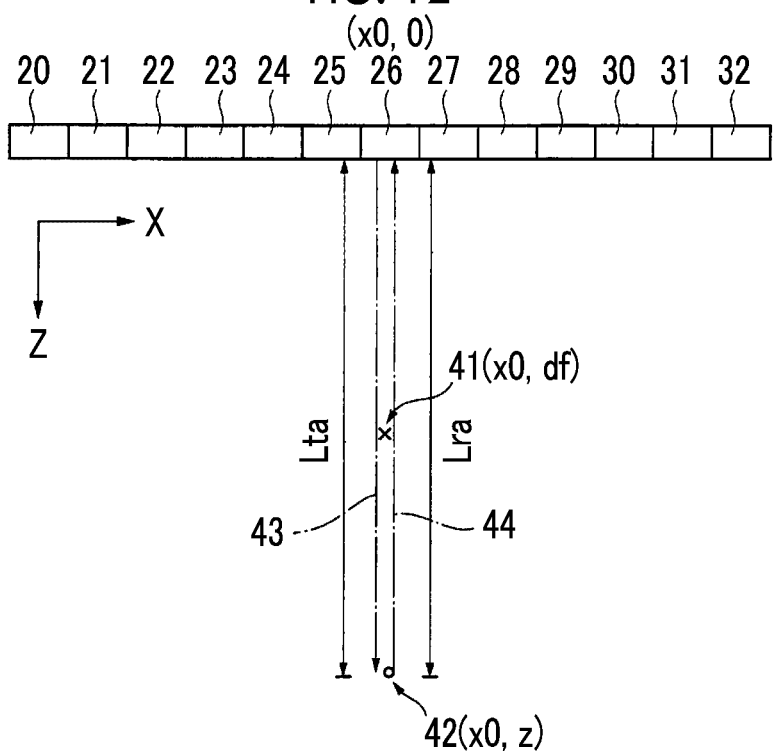
FIG. 12 shows the transmission of ultrasound pulses and the reception of ultrasound echoes.

FIG. 12 shows the ultrasound pulse 43 and the ultrasound echo 44 in a case where there is no positional deviation in one direction between the focusing position 41 and the observation target position 42 as shown in FIG. 6.

It is assumed that one direction is an X direction and a direction perpendicular to the one direction is a Z direction. It is assumed that the X and Z coordinates of the ultrasound transducer 26 located immediately above the focusing position 41 are $(X, =(x0, 0)$, the coordinates of the focusing position 41 are $(X, Z)=(x0, df)$, and the coordinates of the observation target position 42 are (X, Z)=(x0, z). In a case where there is no positional deviation in one direction between the focusing position 41 and the observation target position 42, the length Lta of a transmission path until the ultrasound pulse 43 transmitted from the ultrasound transducer 26 reaches the observation target position 42 through the focusing position 41 is equal to the length Lra of a receiving path until the ultrasound echo 44 reflected from the observation target position 42 returns to the ultrasound transducer 26 from the observation target position 42. Accordingly, since Lta=Lra=z is satisfied, a propagation distance Lua obtained by adding up the propagation distance Lta of the ultrasound pulse 43 and the propagation distance Lra of the ultrasound echo 44 is Lua=Lta+Lra=2z. By dividing the propagation distance Lua obtained as described above by sound speed, the propagation time of the ultrasound pulse 43 and the ultrasound echo 44 in a case where there is no positional deviation is obtained.

Figure 13:
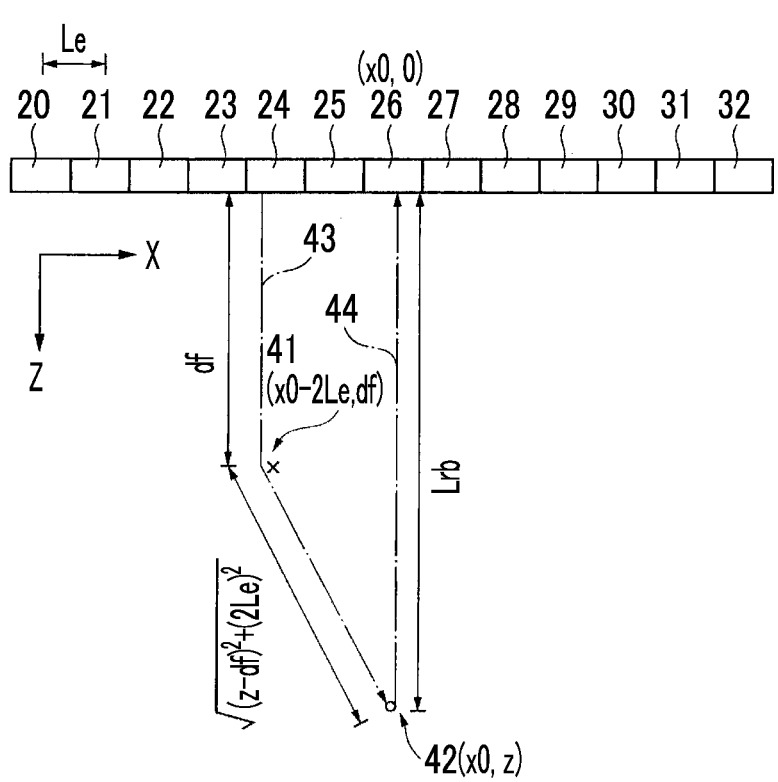
FIG. 13 shows the transmission of ultrasound pulses and the reception of ultrasound echoes.

FIG. 13 shows the ultrasound pulse 43 and the ultrasound echo 44 in a case where there is a positional deviation in one direction between the focusing position 41 and the observation target position 42 as shown in FIG. 2.

The focusing position 41 is shifted from the observation target position 42 by the distance between two ultrasound transducers in one direction. Assuming that the distance between ultrasound transducers is Le, the X and Z coordinates of the focusing position 41 are expressed by (X, Z)=(x0–2Le, df). The ultrasound pulse 43 transmitted from the ultrasound transducer 24 is transmitted to the observation target position 42 through the focusing position 41. The length Ltb of the transmission path of the ultrasound pulse 43 transmitted from the ultrasound transducer 24 is a sum of the distance df from the ultrasound transducer 24 to the focusing position 41 and a distance $\sqrt{(z-df)^2+(2Le)^2}$ from the focusing position 41 to the observation target position 42. In addition, the length Lrb of the receiving path until the ultrasound echo 44 reflected from the observation target position 42 reaches the ultrasound transducer 26 is Lrb=z. The propagation distance Lub obtained by adding up the propagation distance Ltb of the ultrasound pulse 43 and the propagation distance Lrb of the ultrasound echo 44 is Lub=Ltb+Lrb=$\sqrt{(z-df)^2+(2Le)^2}$+z. By dividing the propagation distance Lub obtained as described above by sound speed, the propagation time of the ultrasound pulse 43 and the ultrasound echo 44 in a case where there is a positional deviation is obtained.

From the difference between the propagation time in a case where there is no positional deviation and the propagation time in a case where there is a positional deviation, the delay time to be corrected in the first correction is calculated. It is needless to say that the delay time can be similarly calculated in the cases of positional deviation shown in FIGS. 4, 8, and 10 as well as in the case of positional deviation shown in FIG. 2.

Also for the ultrasound echo signal groups g52, g54, and g55 in which one-direction positional deviation occurs between the focusing position 41 and the observation target position 42 as in FIGS. 5, 9, and 11, positional deviation correction is performed by the ultrasound echo data processing device 10, and ultrasound echo signal groups g62, g64, and g65 for which the positional deviation has been corrected are obtained.

Then, the ultrasound echo signal groups g61, g62, g64, and g65 for which the positional deviation has been corrected and the ultrasound echo signal group g53 without positional deviation are superimposed by the ultrasound echo data processing device 10 so that the ultrasound echo signals output from the same ultrasound transducer are added up.

The superimposed ultrasound echo signals 69 to 79 are supplied to a phasing addition device 11.

Figure 14:
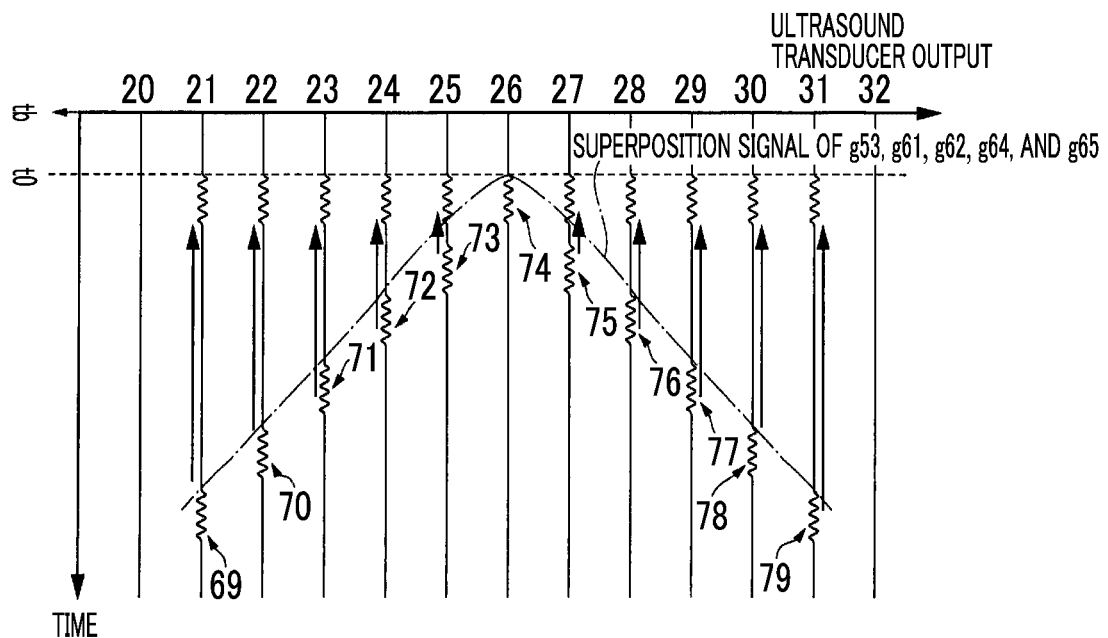
FIG. 14 shows a part of processing for phasing addition.
Figure 15:
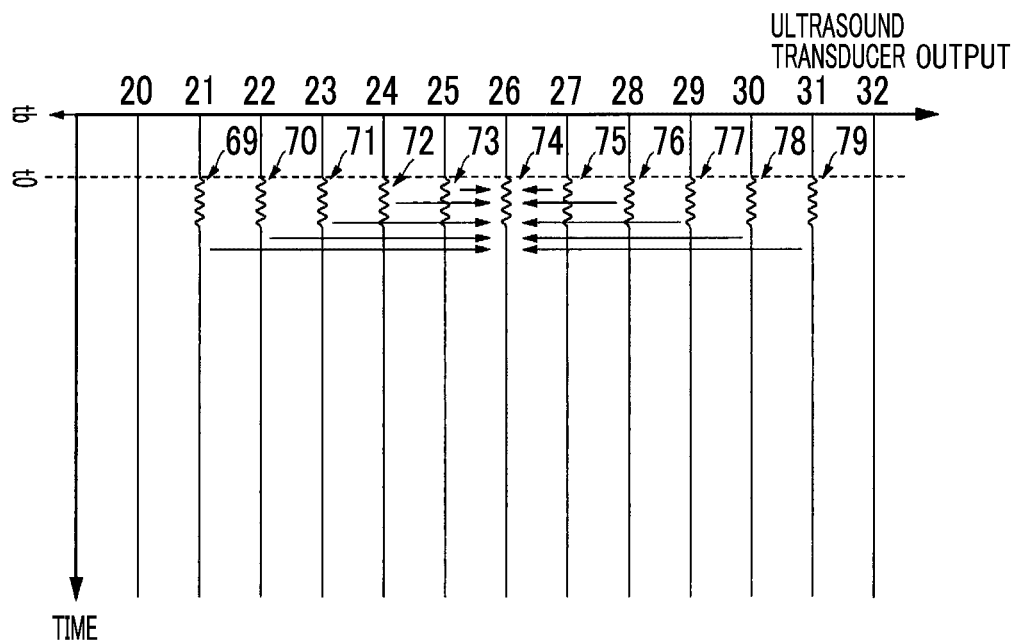
FIG. 15 shows a part of processing for phasing addition.

FIGS. 14 and 15 show a state in which the superimposed ultrasound echo signals 69 to 79 are phased and added.

Referring to FIG. 14, output time correction for the superimposed ultrasound echo signals 69 to 79 is performed by the phasing addition device 11 so that the output time of the superimposed ultrasound echo signals 69 to 79 becomes the same as the output timing of the ultrasound echo signal 74 that is first output from the ultrasound transducer 26 at time t0.

Then, referring to FIG. 15, the ultrasound echo signals 69 to 79 after the output time correction are phased and added by the phasing addition device 11 so as to be superimposed at the position of the ultrasound transducer 26 on the extension line of the observation target position 42. The S/N ratio is improved by performing phasing addition.

Here, the ultrasound echo signal groups g61, g62, g64, and g65 for which the positional deviation has been corrected and the ultrasound echo signal group g53 for which no positional deviation has been corrected are superimposed after being subjected to delay time correction. However, the order is not limited thereto. That is, the ultrasound echo signal groups g61, g62, g64, and g65 for which the positional deviation has been corrected and the ultrasound echo signal group g53 for which no positional deviation has been corrected may be subjected to delay time correction after a piece of superposition data is obtained. In addition, at least some of the ultrasound echo signal groups g61, g62, g64, and g65 for which the positional deviation has been corrected and the ultrasound echo signal group g53 for which no positional deviation has been corrected may be superimposed after being weighted by the ultrasound echo data processing device 10 (a weighting device).

Referring to FIG. 1, ultrasound echo data after phasing addition is input to a digital scan converter (DSC) 13.

The DSC 13 performs raster conversion into image data according to the normal scan method of television signals. The image data output from the DSC 13 is subjected to image processing, such as gradation processing, by an image generating device 14. A second B-mode image (second acoustic wave image) showing the brightness of the subject is generated from the superposition signal (a second acoustic wave image generation device). Image data output from the image generating device 14 is supplied to a display control device 16, and a color-mode ultrasound image is displayed on the display screen of a display device 17. The image data output from the image generating device 14 is also supplied to an image memory 15, and the image data indicating an ultrasound image is stored in the image memory 15. By supplying the image data stored in the image memory 15 to the display control device 16, an ultrasound image (second B-mode image) is displayed on the display screen of the display device 17.

In the case of generating the second B-mode image, since the positional deviation correction is not performed, the first B-mode image showing the brightness of the cross section of the subject is generated, from an acoustic wave echo output from each ultrasound transducer after the ultrasound transducer receives the acoustic wave echo at the observation target position of the subject obtained based on the driving of the ultrasound transducer (acoustic wave transducer) by the control device 2 (a driving device), by the phasing addition device 11 and the DSC 13 (a first acoustic wave image generation device).

Figure 16:
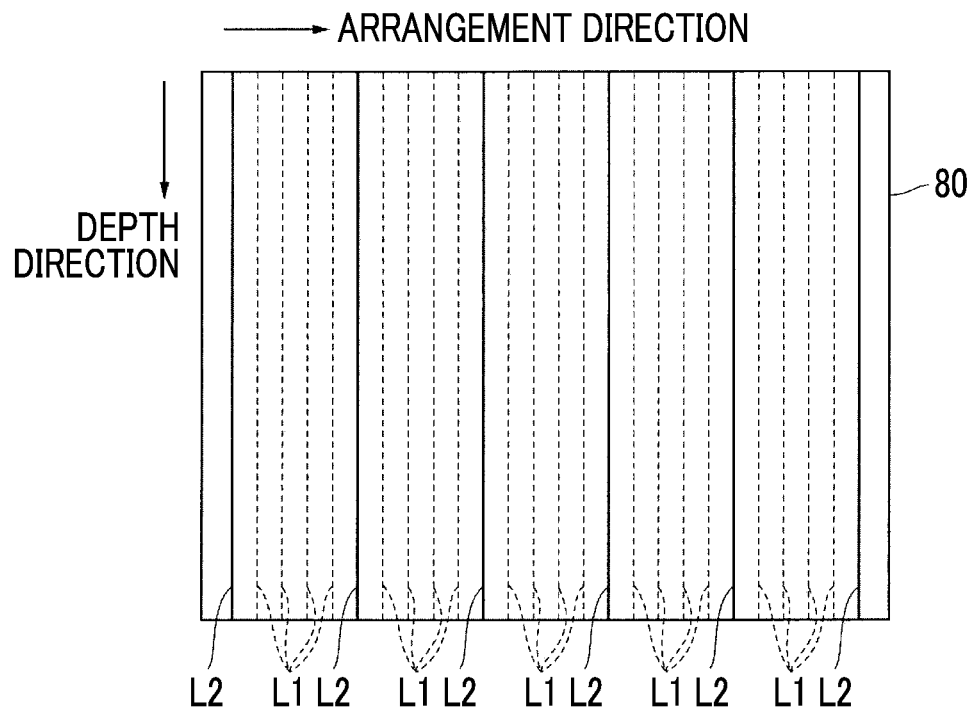
FIG. 16 is an example of a first B-mode image.

FIG. 16 shows a first B-mode image.

Since a first B-mode image 80 shown in FIG. 16 is mainly for explaining the number of lines in the horizontal direction, images of organs or the like that are observation targets, are omitted.

The vertical direction of the first B-mode image 80 corresponds to the depth direction of the subject, and the horizontal direction corresponded to the arrangement direction of ultrasound transducers included in the ultrasound probe 6. In the first B-mode image 80, a number of lines L1 and L2 are shown. The lines L1 and L2 correspond to ultrasound transducers. The total number of lines L1 and L2 is equal to the number of ultrasound transducers included in the ultrasound probe 6.

In contrast, the multi-line processing described above is performed every several lines. For example, multi-line processing is performed for each line L2 shown by the solid line, and multi-line processing is not performed in the line L1 shown by the dotted line. That is, in a situation where positional deviation correction is not necessary as shown in FIG. 6, multi-line processing is performed in a case where the focusing position 41 is present on the line L2, and no multi-line processing is performed in a case where the focusing position 41 is present on the line L1. Correction of positional deviation and superposition of the ultrasound echo signal (acoustic wave echo signal) for which the positional deviation has been corrected and the ultrasound echo signal without positional deviation are performed every one or more ultrasound transducers (acoustic wave transducers) (for example, every 5 lines, every 10 lines, and every 20 lines) in one direction (arrangement direction). In addition, the number of ultrasound transducers (acoustic wave transducers) driven in a case where the first B-mode image is generated is different from the number of ultrasound transducers (acoustic wave transducers) driven in a case where the correction of positional deviation is performed.

Figure 17:
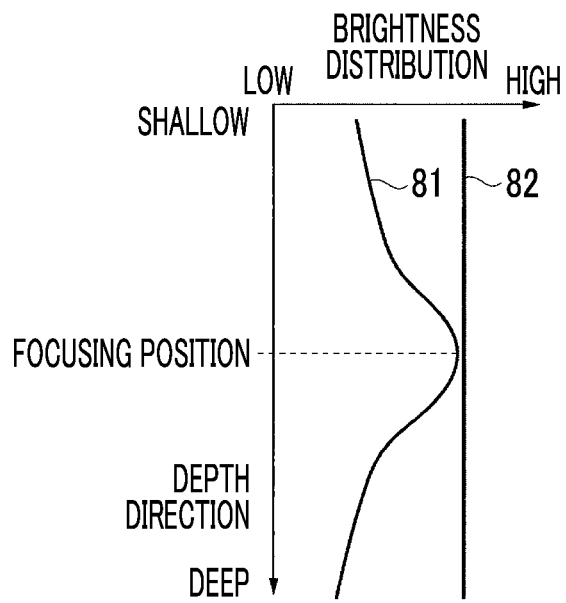
FIG. 17 shows first brightness information and second brightness information.

FIG. 17 shows the relationship between the brightness distribution and the depth direction.

The horizontal direction indicates the brightness distribution, and the brightness level increases toward the right side in FIG. 17. The vertical direction indicates the depth direction, and the depth for the subject increases toward the lower side in FIG. 17.

The brightness information (first brightness information) of the first B-mode image 80 is shown by reference numeral 81. The brightness information (second brightness information) of the second B-mode image obtained by multi-line processing is shown by reference numeral 82. The first brightness information is generated when the control device 2 calculates an average brightness value for each depth from the first B-mode image 80 generated by the image generating device 14 (a first brightness information generation device). In addition, in a case where the second B-mode image is generated by the image generating device 14, the second brightness information is generated when the control device 2 calculates an average brightness value for each depth from the generated second B-mode image (a second brightness information generation device). Even in a case where no second B-mode image is generated, an average brightness value is calculated for each depth from data for generating the second B-mode image, and the second brightness information is generated by the control device 2, The second brightness information indicating the brightness in the depth direction of the subject is generated from the superposition signal obtained by superimposing the acoustic wave echo signal (ultrasound echo data) for which the positional deviation has been corrected and the acoustic wave echo signal without positional deviation.

The first B-mode image 80 has a high brightness in the vicinity of the focusing position 41, but has a relatively low brightness in a region other than the vicinity of the focusing position 41. In contrast, the second B-mode image has a fixed brightness regardless of the depth.

In the present embodiment, based on the first brightness information and the second brightness information that have been generated, the first B-mode image (first acoustic wave image) is corrected by the control device 2 (a brightness correction device). Accordingly, the brightness of the first B-mode image becomes a fixed brightness similar to the brightness of the second B-mode image. In the related art, in the case of simply trying to perform correction to obtain a fixed brightness, if there is a place where the brightness is extremely high due to artifacts or the like, it is determined that the brightness at the depth is high and the brightness of a dark organ does not rise. For this reason, brightness correction could not be performed sufficiently. If an image obtained by superimposing the acoustic wave echo signal group for which the positional deviation has been corrected and the acoustic wave echo signal group for which no positional deviation has been corrected is used as in the present embodiment, the brightness of artifacts is also included in the brightness information (second brightness information) of the image obtained by the superposition. Accordingly, brightness correction can be appropriately performed.

A ratio between first brightness information 81 and second brightness information 82 is calculated by the control device 2 for each depth, and the ratio becomes a correction coefficient for correcting the first B-mode image (a correction coefficient calculation device).

Figure 18:
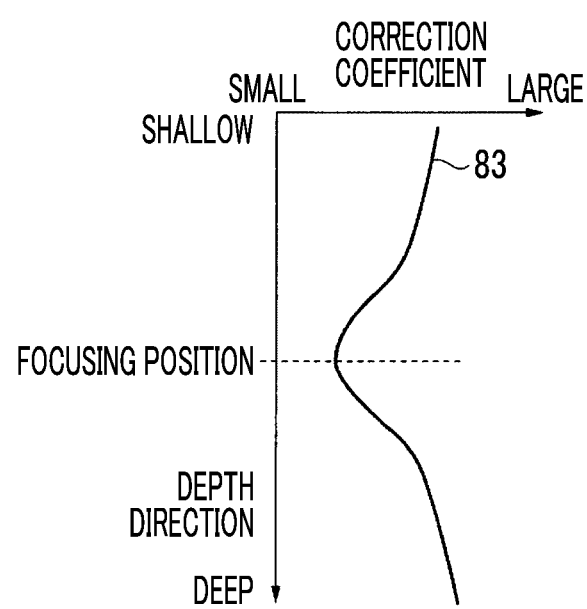
FIG. 18 shows a correction coefficient.

FIG. 18 is an example of the correction coefficient.

In FIG. 18, the horizontal direction indicates a value of the correction coefficient, and the value of the correction coefficient increases toward the right side. In FIG. 18, the vertical direction indicates the depth direction of the subject, and the depth increases toward the lower side.

The correction coefficient is approximately 1 in the vicinity of the focusing position, and is a relatively large value in other places. The first B-mode image is corrected using such a correction coefficient. Accordingly, the first B-mode image has a fixed brightness. The first B-mode image whose brightness has been corrected in this manner is displayed on the display screen of the display device 17.

The correction coefficient may be calculated based on the focusing position, or may be calculated without using the focusing position.

In a case where the brightness of the corrected first B-mode image is not fixed, further correction may be performed to have a fixed brightness. In order that the magnitude of the brightness does not change even if the focusing position is changed, the brightness may be standardized as the brightness of an image portion corresponding to the focusing position at all times, or the brightness of the corrected first B-mode image may be the same. Also in the switching of the frequency of sound waves from the ultrasound probe, mode switching, and the like, the magnitude of the brightness of the corrected first B-mode image may not be changed.

Figure 19:
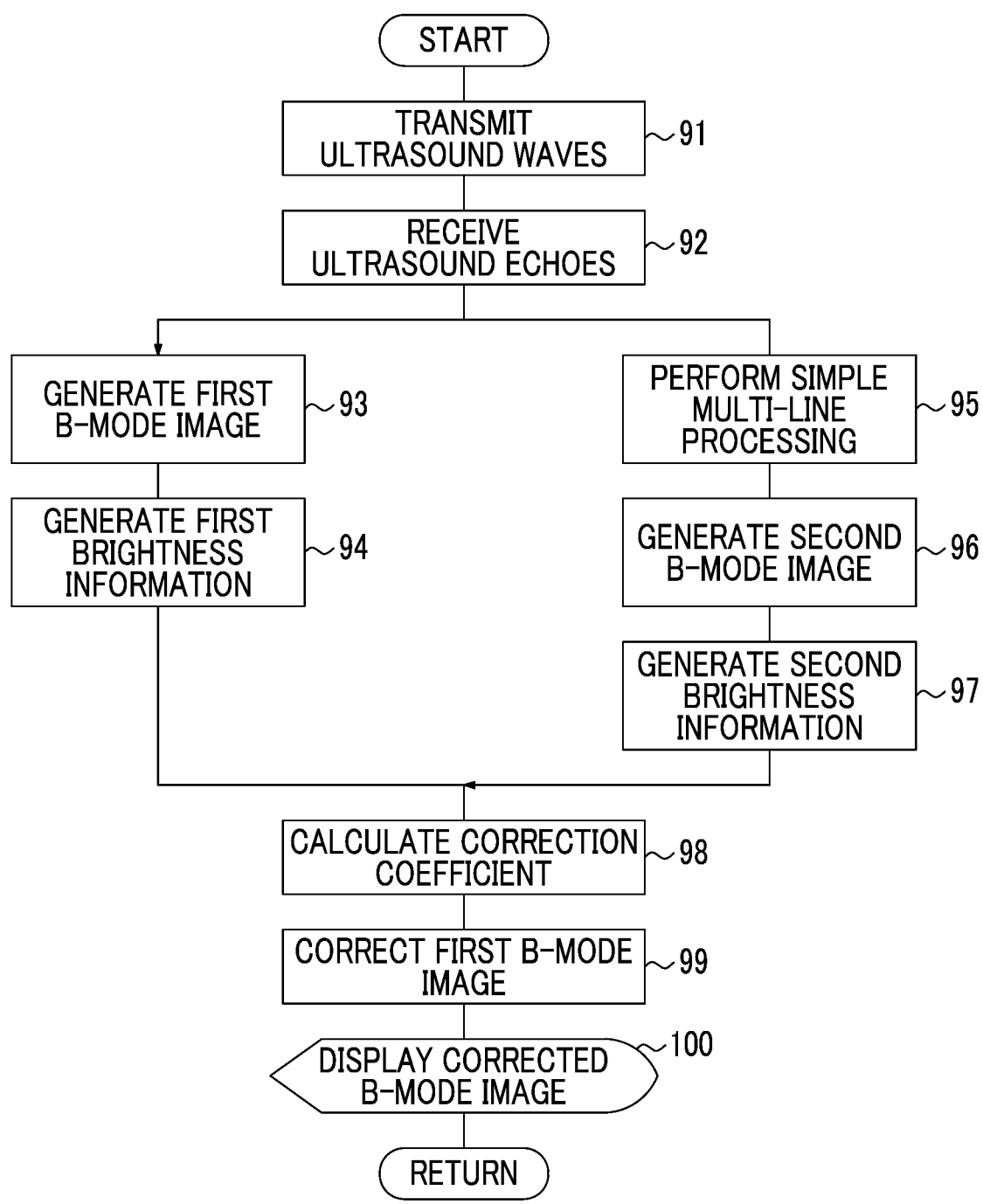
FIG. 19 is a flowchart showing the procedure of the processing of the ultrasound diagnostic apparatus.

FIG. 19 is a flowchart showing the procedure of the processing of the ultrasound diagnostic apparatus 1.

Ultrasound waves are transmitted toward the subject from the ultrasound probe 6 (step 91), and ultrasound echoes are received (step 92). A first B-mode image is generated (step 93), and the first brightness information 81 is generated (step 94). Multi-line processing (simple multi-line processing) is performed every several lines (step 95), and the second B-mode image is generated (step 96). In addition, the second brightness information 82 is generated (step 97).

A correction coefficient 83 is calculated from the first brightness information 81 and the second brightness information 82 that have been generated (step 98), and the brightness of the first B-mode image is corrected using the calculated correction coefficient 83 (step 99). The corrected first B-mode image is displayed on the display screen of the display device 17 (step 100).

What is claimed is:

1. An acoustic wave image generating apparatus, comprising:
    an acoustic wave probe in which a plurality of acoustic wave transducers are arranged in at least one direction;
    a processor circuitry for performing processing for transmitting a plurality of acoustic waves, which converge on a focusing position, to a subject from the acoustic wave transducers to be driven while sequentially updating the acoustic wave transducers to be driven;
    a digital scan converter for generating a first acoustic wave image, which shows a brightness of a cross section of the subject, from a plurality of acoustic wave echo signals that are output from the acoustic wave transducers due to the acoustic wave transducers receiving acoustic wave echoes at an observation target position of the subject obtained based on the driving of the acoustic wave transducers by the processor circuitry;
    the processor circuitry further for generating first brightness information indicating a brightness of the first acoustic wave image in a depth direction of the subject; and
    the processor circuitry further for directly correcting, for the one of the plurality of acoustic wave echo signals having a positional deviation between the focusing position and the observation target position in the one direction, the positional deviation of the one direction according to positions of the acoustic wave transducers driven by the processor circuitry;
    wherein the processor circuitry generates second brightness information, which indicates a brightness in the depth direction of the subject, from a superposition signal obtained by superimposing the one of the plurality of acoustic wave echo signals for which the positional deviation of the one direction has been corrected by the processor circuitry and the one of the plurality of acoustic wave echo signals without the positional deviation of the one direction, calculates a ratio between the first brightness information and the second brightness information for each depth, and uses the ratio as a correction coefficient, and
    the processor circuitry further for, for each depth, correcting a brightness of the first acoustic wave image generated by the digital scan converter using the respective correction coefficient that was calculated.

2. The acoustic wave image generating apparatus according to claim 1,
    wherein the processor circuitry comprises correction coefficient calculation device for calculating the correction coefficient, which is for correcting the brightness of the first acoustic wave image generated by the digital scan converter, based on the first brightness information generated by the processor circuitry and the second brightness information generated by the processor circuitry, and
    the brightness of the first acoustic wave image generated by the digital scan converter is corrected using the correction coefficient calculated by the correction coefficient calculation device.

3. The acoustic wave image generating apparatus according to claim 1,
    wherein the number of acoustic wave transducers driven in a case where the first acoustic wave image is generated by the digital scan converter is different from the number of acoustic wave transducers driven in a case where correction of positional deviation is performed by the processor circuitry.

4. The acoustic wave image generating apparatus according to claim 1,
    wherein the positional deviation correction of the digital scan converter and superposition of the acoustic wave echo signal for which the positional deviation has been corrected and the acoustic wave echo signal without the positional deviation are performed every one or more of the ultrasound transducers in the one direction.

5. The acoustic wave image generating apparatus according to claim 1,
    wherein at least some of the acoustic wave echo signals for which the positional deviation has been corrected and acoustic wave echo signals without the positional deviation are superimposed after being weighted.

6. The acoustic wave image generating apparatus according to claim 2,
    wherein the correction coefficient calculation device calculates the correction coefficient, based on a brightness of a portion corresponding to the focusing position, in the first acoustic wave image generated by the digital scan converter.

7. The acoustic wave image generating apparatus according to claim 1, further comprising:
    a second acoustic wave image generation device for generating a second acoustic wave image showing a brightness of the subject from the superposition signal.

8. A control method of an acoustic wave image generating apparatus comprising an acoustic wave probe in which a plurality of acoustic wave transducers are arranged in at least one direction, comprising:
    causing a processor circuitry to perform processing for transmitting a plurality of acoustic waves, which converge on a focusing position, to a subject from the acoustic wave transducers to be driven while sequentially updating the acoustic wave transducers to be driven;
    causing an acoustic wave image generation device to generate an acoustic wave image, which shows a brightness of a cross section of the subject, from a plurality of acoustic wave echo signals that are output from the acoustic wave transducers due to the acoustic wave transducers receiving acoustic wave echoes at an observation target position of the subject obtained based on the driving of the acoustic wave transducers by the processor circuitry;
    causing the processor circuitry to generate first brightness information indicating a brightness of the first acoustic wave image in a depth direction of the subject;
    causing a digital scan converter to directly correct, for the one of the plurality of acoustic wave echo signals having a positional deviation between the focusing position and the observation target position in the one direction, the positional deviation according to positions of the acoustic wave transducers driven by the processor circuitry;

causing the processor circuitry to generate second brightness information, which indicates a brightness in the depth direction of the subject, from a superposition signal obtained by superimposing the one of the plurality of acoustic wave echo signals for which the positional deviation has been corrected by the digital scan converter and the one of the plurality of acoustic wave echo signals without the positional deviation, calculate a ratio between the first brightness information and the second brightness information for each depth, and use the ratio as a correction coefficient; and causing the processor circuitry to, for each depth, correct a brightness of the acoustic wave image generated by the acoustic wave image generation device using the respective correction coefficient that was calculated.

9. An acoustic wave image generating apparatus, comprising:

an acoustic wave probe in which a plurality of acoustic wave transducers are arranged in at least one direction;

a processor circuitry for performing processing for transmitting a plurality of acoustic waves, which converge on a focusing position, to a subject from the acoustic wave transducers to be driven while sequentially updating the acoustic wave transducers to be driven;

a digital scan converter for generating a first acoustic wave image, which shows a brightness of a cross section of the subject, from a plurality of acoustic wave echo signals that are output from the acoustic wave transducers due to the acoustic wave transducers receiving acoustic wave echoes at an observation target position of the subject obtained based on the driving of the acoustic wave transducers by the processor circuitry;

the processor circuitry further for generating first brightness information indicating a brightness of the first acoustic wave image in a depth direction of the subject; and the processor circuitry further for directly correcting, for the one of the plurality of acoustic wave echo signals having a positional deviation between the focusing position and the observation target position in the one direction, the positional deviation of the one direction according to positions of the acoustic wave transducers driven by the processor circuitry;

wherein the processor circuitry generates second brightness information, which indicates a brightness in the depth direction of the subject, from a superposition signal obtained by superimposing the one of the plurality of acoustic wave echo signals for which the positional deviation of the one direction has been corrected by the processor circuitry and the one of the plurality of acoustic wave echo signals without the positional deviation of the one direction, and, for each depth, calculates a correction coefficient which is 1 in the vicinity of the focusing position and more than 1 in other places, and the processor circuitry further for, for each depth, correcting a brightness of the first acoustic wave image generated by the digital scan converter using the respective correction coefficient that was calculated.

10. A control method of an acoustic wave image generating apparatus comprising an acoustic wave probe in which a plurality of acoustic wave transducers are arranged in at least one direction, comprising:

causing a processor circuitry to perform processing for transmitting a plurality of acoustic waves, which converge on a focusing position, to a subject from the acoustic wave transducers to be driven while sequentially updating the acoustic wave transducers to be driven;

causing an acoustic wave image generation device to generate a first acoustic wave image, which shows a brightness of a cross section of the subject, from a plurality of acoustic wave echo signals that are output from the acoustic wave transducers due to the acoustic wave transducers receiving acoustic wave echoes at an observation target position of the subject obtained based on the driving of the acoustic wave transducers by the processor circuitry;

causing the processor circuitry to generate first brightness information indicating a brightness of the first acoustic wave image in a depth direction of the subject; and causing a digital scan converter to directly correct, for the one of the plurality of acoustic wave echo signals having a positional deviation between the focusing position and the observation target position in the one direction, the positional deviation of the one direction according to positions of the acoustic wave transducers driven by the processor circuitry;

causing the processor circuitry to generate second brightness information, which indicates a brightness in the depth direction of the subject, from a superposition signal obtained by superimposing the one of the plurality of acoustic wave echo signals for which the positional deviation of the one direction has been corrected by the processor circuitry and the one of the plurality of acoustic wave echo signals without the positional deviation of the one direction, and, for each depth, calculates a correction coefficient which is 1 in the vicinity of the focusing position and more than 1 in other places, and the processor circuitry further for, for each depth, correcting a brightness of the first acoustic wave image generated by the digital scan converter using the respective correction coefficient that was calculated.

* * * * *